United States Patent
Schofield et al.

(10) Patent No.: US 6,274,352 B1
(45) Date of Patent: *Aug. 14, 2001

(54) METHODS FOR DIAGNOSING AND ASSESSING A PREDISPOSITION TO BIPOLAR AFFECTIVE DISORDER

(75) Inventors: Peter Robert Schofield, Marsfield; Philip Bowden Mitchell, Epping; Linda Jacqueline Adams, Mortdale, all of (AU)

(73) Assignee: Garvan Institute of Medical Research, Darlinghurst (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/230,804
(22) PCT Filed: Jun. 10, 1998
(86) PCT No.: PCT/AU98/00439
 § 371 Date: Feb. 19, 1999
 § 102(e) Date: Feb. 19, 1999
(87) PCT Pub. No.: WO98/56947
 PCT Pub. Date: Dec. 17, 1998

(30) Foreign Application Priority Data

Jun. 10, 1997 (AU) .................................. PO 7268

(51) Int. Cl.⁷ .................. C12P 19/34; C12Q 1/68; G01N 33/00; C07H 21/02; C07H 21/04

(52) U.S. Cl. .................. 435/91.1; 435/6; 435/91.2; 436/94; 536/23.1; 536/24.3; 536/24.31
(58) Field of Search .................. 435/6, 91.1, 91.2, 435/320.1; 204/405; 536/23.1, 24.3, 24.33, 25.3; 436/94

(56) References Cited

FOREIGN PATENT DOCUMENTS

| 9734928 | 9/1997 | (WO) . |
| 9737043 | 10/1997 | (WO) . |
| 9818963 | 5/1998 | (WO) . |

OTHER PUBLICATIONS

Adams et al., *American Journal of Human Genetics*, vol. 62, Apr. 1998, pp. 1084–1091.

Blackwood et al., *Nature Genetics*, vol. 12, 1996, pp. 427–430.

(List continued on next page.)

Primary Examiner—Ethan Whisendat
Assistant Examiner—Frank Lu
(74) Attorney, Agent, or Firm—Rothwell, Figg, Ernst & Manbeck

(57) ABSTRACT

A method of assessing an individual's predisposition to bipolar affective disorder comprises determining the presence of one or more bipolar affective disorder-linked markers on chromosome 4 or analyzing allelic variation in relation to a bipolar affective disorder susceptibility gene on chromosome 4.

4 Claims, 1 Drawing Sheet

OTHER PUBLICATIONS

Detara–Wadleigh et al., *American Journal of Medical Genetics*, vol. 74, May 1997, pp. 254–262.

Van Deutekom et al., Identification of the first gene (FRG1) from the FSHD region on human chromosome 4q 35. Human Mol. Genet., 5, 581–590, 1996.*

Van Deutekom et al., Search for the FSHD gene using cDNA selection in a region spanning 100 kb on chromosome 4q35. Muscle & Nerve, Supplement 2, S19–S26, 1995.*

Gershon et al., Maternal inheritance and chromosome 18 allele sharing in unilineal biopolar illness pedigrees. Am. J. Med.. Genet. 67, 202–207, 1996.*

Detera–Wadleigh et al., Affected–sib–pair analyses reveal support of prior evidence for a susceptibility locus for bipolar disorder, on 21q. Am. J. Hum. Genet. 58, 1279–1285, 1996.*

Detera–Wadleigh et al., A high–density genome scan detects evidence for a bipolar–disorder susceptibility locus on 13q32 and other potential loci on 1q32 and 18p11.2. Proc. Natl. Acad. Sci. USA 96, 5604–5609, May 1999.*

Wijmenga et al., Chromosome 4q DNA rearrangements associated with faciioscapulohumeral muscular dystrophy. Nature Genetics 2, 26–30, 1992.*

Kwok et al., Nonparametric simulation–based statistical analyses for bipolar affective disorder locus on chromosome 21q22.3. Am. J. Med. Genet. 88, 99–102, Feb. 1999.*

* cited by examiner

SEQUENCE LISTING

<160> NUMBER OF SEQ ID NOS: 30

<210> SEQ ID NO 1
<211> LENGTH: 23
<212> TYPE: DNA
<213> ORGANISM: Homo sapiens

<400> SEQUENCE: 1
aatccctggg tacattatat ttg     23

<210> SEQ ID NO 2
<211> LENGTH: 25
<212> TYPE: DNA
<213> ORGANISM: Homo sapiens

<400> SEQUENCE: 2
cagacattct ttattcttta cctcc     25

<210> SEQ ID NO 3
<211> LENGTH: 23
<212> TYPE: DNA
<213> ORGANISM: Homo sapiens

<400> SEQUENCE: 3
cctcatggta ggttaatccc acg     23

<210> SEQ ID NO 4
<211> LENGTH: 20
<212> TYPE: DNA
<213> ORGANISM: Homo sapiens

<400> SEQUENCE: 4
tattgaatgc ccgccatttg     20

<210> SEQ ID NO 5
<211> LENGTH: 25
<212> TYPE: DNA
<213> ORGANISM: Homo sapiens

<400> SEQUENCE: 5
atacactgca tccatatata caagg     25

<210> SEQ ID NO 6
<211> LENGTH: 20
<212> TYPE: DNA
<213> ORGANISM: Homo sapiens

<400> SEQUENCE: 6
acattgtgaa atgaccacag     20

<210> SEQ ID NO 7
<211> LENGTH: 25
<212> TYPE: DNA
<213> ORGANISM: Homo sapiens

```
<400> SEQUENCE: 7
tgaaattcta ttgaccaatg atgtg                                          25

<210> SEQ ID NO 8
<211> LENGTH: 22
<212> TYPE: DNA
<213> ORGANISM: Homo sapiens

<400> SEQUENCE: 8
tagcacctgg atttaccatg ac                                             22

<210> SEQ ID NO 9
<211> LENGTH: 22
<212> TYPE: DNA
<213> ORGANISM: Homo sapiens

<400> SEQUENCE: 9
tttgtttggt ctatcaaaag tc                                             22

<210> SEQ ID NO 10
<211> LENGTH: 16
<212> TYPE: DNA
<213> ORGANISM: Homo sapiens

<400> SEQUENCE: 10
caagatgtgc agtggg                                                    16

<210> SEQ ID NO 11
<211> LENGTH: 19
<212> TYPE: DNA
<213> ORGANISM: Homo sapiens

<400> SEQUENCE: 11
ggtccagtaa gaggacagt                                                 19

<210> SEQ ID NO 12
<211> LENGTH: 19
<212> TYPE: DNA
<213> ORGANISM: Homo sapiens

<400> SEQUENCE: 12
tgggtaaaga gtgaggctg                                                 19

<210> SEQ ID NO 13
<211> LENGTH: 18
<212> TYPE: DNA
<213> ORGANISM: Homo sapiens

<400> SEQUENCE: 13
agtattgcag tgcttggg                                                  18

<210> SEQ ID NO 14
<211> LENGTH: 20
<212> TYPE: DNA
<213> ORGANISM: Homo sapiens

<400> SEQUENCE: 14
catccacagg ggacacattc                                                20

<210> SEQ ID NO 15
<211> LENGTH: 24
<212> TYPE: DNA
<213> ORGANISM: Homo sapiens
```

```
<400> SEQUENCE: 15
ggtctgatga aaatgttctc aagc                                              24

<210> SEQ ID NO 16
<211> LENGTH: 24
<212> TYPE: DNA
<213> ORGANISM: Homo sapiens

<400> SEQUENCE: 16
tagactgggt tgttagggac tctc                                              24

<210> SEQ ID NO 17
<211> LENGTH: 21
<212> TYPE: DNA
<213> ORGANISM: Homo sapiens

<400> SEQUENCE: 17
acttgtgata tatacctgcc g                                                 21

<210> SEQ ID NO 18
<211> LENGTH: 20
<212> TYPE: DNA
<213> ORGANISM: Homo sapiens

<400> SEQUENCE: 18
tgtgagagca gaatgttgag                                                   20

<210> SEQ ID NO 19
<211> LENGTH: 21
<212> TYPE: DNA
<213> ORGANISM: Homo sapiens

<400> SEQUENCE: 19
ccatttcagt gtctgtgact a                                                 21

<210> SEQ ID NO 20
<211> LENGTH: 18
<212> TYPE: DNA
<213> ORGANISM: Homo sapiens

<400> SEQUENCE: 20
ggaagccaat tcctcata                                                     18

<210> SEQ ID NO 21
<211> LENGTH: 20
<212> TYPE: DNA
<213> ORGANISM: Homo sapiens

<400> SEQUENCE: 21
acacagcaca gtttgtttga                                                   20

<210> SEQ ID NO 22
<211> LENGTH: 18
<212> TYPE: DNA
<213> ORGANISM: Homo sapiens

<400> SEQUENCE: 22
gacctgccta agcctttg                                                     18

<210> SEQ ID NO 23
<211> LENGTH: 20
<212> TYPE: DNA
```

-continued

```
<213> ORGANISM: Homo sapiens

<400> SEQUENCE: 23
cttgtttcct gttgagcact                                              20

<210> SEQ ID NO 24
<211> LENGTH: 24
<212> TYPE: DNA
<213> ORGANISM: Homo sapiens

<400> SEQUENCE: 24
gaatgatgta ctgatcaccc agat                                         24

<210> SEQ ID NO 25
<211> LENGTH: 20
<212> TYPE: DNA
<213> ORGANISM: Homo sapiens

<400> SEQUENCE: 25
aatccctagg caaataccat                                              20

<210> SEQ ID NO 26
<211> LENGTH: 22
<212> TYPE: DNA
<213> ORGANISM: Homo sapiens

<400> SEQUENCE: 26
tcttgagtgg ctgaaactac at                                           22

<210> SEQ ID NO 27
<211> LENGTH: 16
<212> TYPE: DNA
<213> ORGANISM: Homo sapiens

<400> SEQUENCE: 27
tcgagatcgt gccatt                                                  16

<210> SEQ ID NO 28
<211> LENGTH: 23
<212> TYPE: DNA
<213> ORGANISM: Homo sapiens

<400> SEQUENCE: 28
ccccaagatt attcttagac ttt                                          23

<210> SEQ ID NO 29
<211> LENGTH: 21
<212> TYPE: DNA
<213> ORGANISM: Homo sapiens

<400> SEQUENCE: 29
agcacaagat tctctaagcc c                                            21

<210> SEQ ID NO 30
<211> LENGTH: 20
<212> TYPE: DNA
<213> ORGANISM: Homo sapiens

<400> SEQUENCE: 30
aaagccaaaa gatgatgcaa                                              20
```

METHODS FOR DIAGNOSING AND ASSESSING A PREDISPOSITION TO BIPOLAR AFFECTIVE DISORDER

FIELD OF THE INVENTION

This invention relates to methods for diagnosing and assessing a predisposition to bipolar affective disorder (BAD).

BACKGROUND TO THE INVENTION

BAD is a condition characterised by mood swings (mania and depression) that affects 1–2% of the population. Twin and adoption studies have shown that this disorder has a strong genetic component. However, it has a complex genetic basis and increased susceptibilty is likely due to the interplay of a number of distinct genes. The identification of a number of positive linkage results at differing chromosomal positions which supports this model of a complex genetic aetiology. Possible susceptibility loci have been reported on chromosomes 4p, 18p, 18q and 21q (Berrettini et al., 1994; Straub et al., 1994; Gurlinig et al., 1995: Stine et al., 1995; Blackwood et al., 1996: De bruyn et al., 1996: Coon et al. 1996; Freimer et al., 1996). However, no predisposing genes have ,et been identified. The present inventors have conducted a 15-cM genome screen of 214 microsatellite markers on 35 individuals from a large Australian pedigree with a history of BAD. Data were analysed by parametric two-point linkage methods using several diagnostic models. Lod scores >1.00 were obtained for 21 markers, with four of these >2.00 for at least one model. The remaining 52 individuals in the family were then genotyped with these four markers and lod scores remained positive for three markers. A more intensive screen was undertaken in these regions with the most positive results being obtained for chromosome 4q35. Using a dominant model of inheritance with 90% maximum age-specific penetrance and including bipolar I, II, schizoaffective/mania and unipolar individuals as affected, a maximum two-point lod score of 2.20 ($\theta$=0.15) at D4S1652 was obtained and a maximum three-point lod score of 3.19 obtained between D4S408 and D4S2924 was obtained. Non-parametric analyses further supported the presence of a predisposing locus on chromosome 4q35. A maximised score of 2.62 (p=0.01) was obtained between D4S1652 and D4S171 using the GENEHUNTER program, and a maximum score of 3.57 (p=0.0002) was obtained at D4S2924 using the affected pedigree member (APM) method. Analysis of a further twenty-three pedigrees suggested the presence of this susceptibility locus in at least three additional families, indicating a predisposing susceptibiliy locus and not a pedigree-specific mutation. The results suggest the presence of a BAD susceptibility locus on chromosome 4q35.

SUMMARY OF THE INVENTION

In a first aspect, the present invention provides a method of assessing an individual's predisposition to bipolar affective disorder (BAD), comprising a step of determining the presence of a BAD-linked marker(s) on chromosome 4.

Preferably, the method comprises determining the presence of a BAD-linked marker(s) at the chromosomal locus 4q35.

The method may involve the determination of a single BAD-linked marker but more preferably, involves the determination of the presence of at least two BAD-linked markers. Preferably, the BAD-linked marker(s) are microsatellite markers. More preferably, the BAD-linked marker(s) are selected from D4S1652, D4S408. D4S171 and D4S2924.

Preferably, the step of determining the presence of a BAD-linked maker(s) comprises PCR amplification and gel electrophoresis to determine the presence of a specific microsatellite allele for a given marker.

In a second aspect the present invention provides a method of assessing an individual's predisposition to bipolar affective disorder (BAD), comprising a step of analysing allelic variation in relation to a BAD susceptibility gene on chromosome 4 of the individual.

Preferably, the method of the second aspect comprises analysing allelic variation at the chromosomal locus 4q35.

Preferably, the step of analysing allelic variation comprises determining microsatellite alleles by PCR amplification and gel electrophoresis.

In a further aspect, the present invention provides a method of diagnosing bipolar affective disorder (BAD) in an individual, comprising a step of determining the presence of a BAD-linked marker(s) on chromosome 4 or, alternatively, analysing allelic variation in relation to a BAD susceptibility gene on chromosome 4.

The invention in the latter aspect may be coupled with similar screens for other susceptibility markers (e.g. markers at chromosomal loci 21q22 (Straub et al., 1994), 18p (Berretini et al., 1994) and 18q (Freimer et al., 1996), and as such may provide a valuable clinical test. An example of such a test is one in which a patient is screened for, say, 12 susceptibility loci. If the test is positive for > say 6, there is a high risk.

The present invention may be used to guide the cloning of the susceptibility gene and the identification of the allelic variation in the susceptibility gene that results in the allellic variant of the gene providing a higher relative risk, to carriers. Testing directly for this allelic variation will be the preferred diagnostic test. The method of the invention may allow identification of drugs that block or enhance the action of this gene is further likely to be of value in the clinical treatment of bipolar affective disorder.

Thus, in a third aspect, the present invention provides an isolated polynulcleotide molecule comprising a BAD susceptibility gene from the human chromosomal locus 4q35.

The terms "comprise", "comprises" and "comprising" as used throughout the specification are intended to refer to the inclusion of a stated step, component or feature or group of steps, components or features with or without the inclusion of a further step, component or feature or group of steps, components or features.

Figure 1:
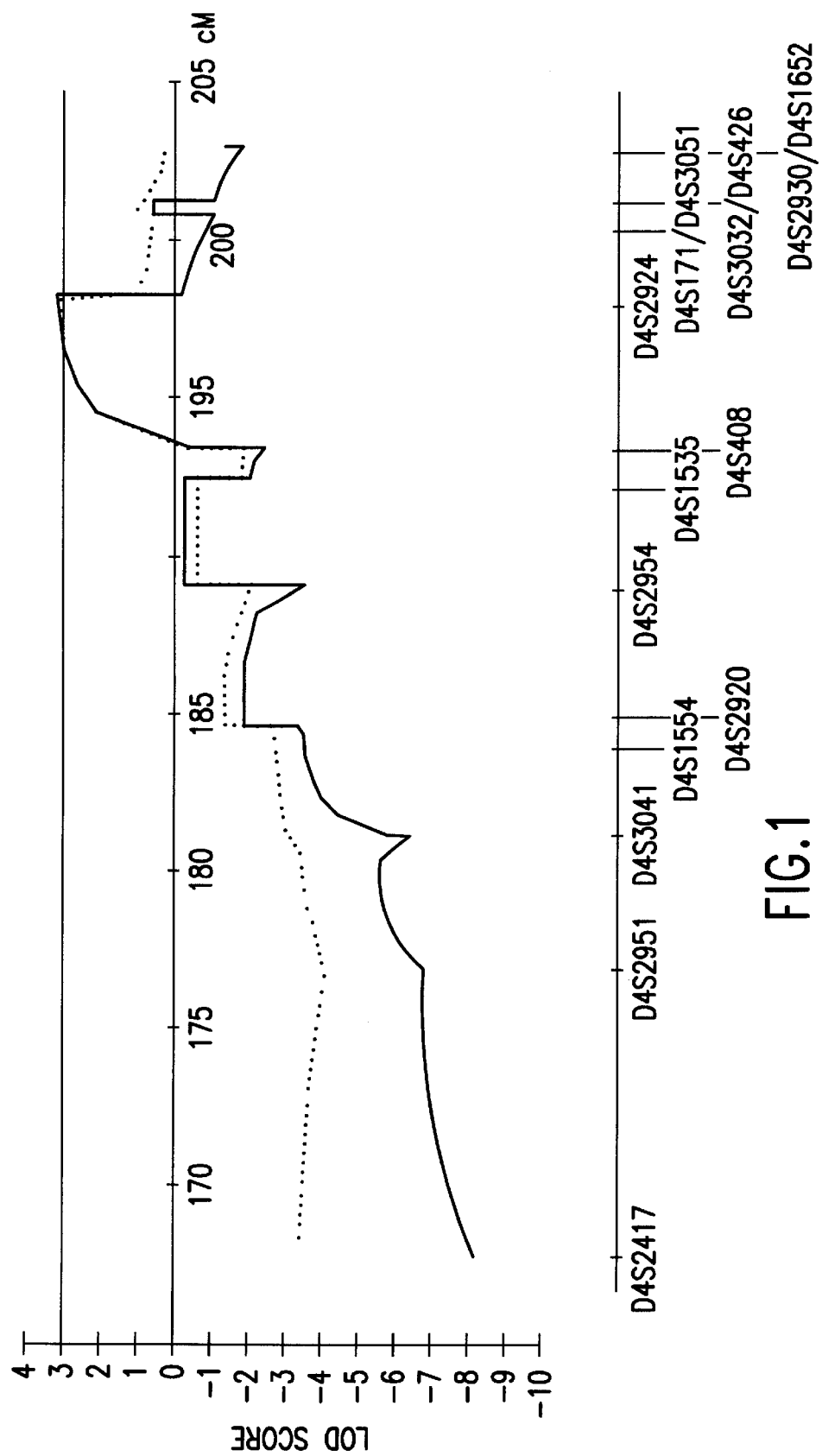
FIG. 1 provides three point LOD scores of 15 markers analyzed of 4q35 using Model II with 90% (solid line) and 60% (dotted line) maximum age-specific penetrance levels.

Detailed Disclosure of the Invention:

Materials and Methods

Families

The families used in this study came from most states of Australia and were identified through a survey of the Mood Disorders Unit, Prince Henry Hospital. Sydney: the New South Wales Depression and Mood Disorders Association: and publicity through articles in popular magazines. These families w, ere assessed using the Diagnostic Interview for Genetic Studies (DIGS) (Nurnberger et al. 1994), and best estimate Research Diagnostic Criteria (RDC) diagnoses were made after independent evaluation of all interviews and records. Individuals whose DNA was used in this study provided appropriate informed consent. Medium to large-sized multigenerational pedigrees were recruited which contained a minimum of 3 affected individuals, at least two of whom were diagnosed with bipolar I.

The family used in the initial genetic screen contains 87 members with available DNA samples, including 11 affected individuals: 5 bipolar I (BPI), 1 schizoaffective/mania (SZ/MA) and 5 recurrent unipolar (UP) (Mitchell et al. 1991). The maximum and average expected lod scores for this family, as determined by SLINK (Ott 1989; Weeks et al. 1990) are 8.64 and 3.95. Ten more pedigrees ascertained in the same manner were typed for markers in the most positive region identified from the genome screen. These pedigrees consisted of 137 individuals for genotyping, including 47 affecteds (22 BPI; 2 SZ/MA; 4 bipolar II (BPII) and 19 UP). The pedigrees have combined maximum and average expected lod scores under the assumption of homogeneity of 19.79 and 8.44 respectively, and maximum and average lod scores under the assumption of heterogeneity of 19.68 and 4.99 respectively, as determined by SLINK. A further sample of 13 pedigrees which contain 182 individuals including 51 affected (30 BPI; 9 SZ/MA; 2 BPII and 10 UP) was also used to test for the presence of linkage.

Genotyping

DNA was extracted from whole blood using standard techniques. Microsatellite markers analysed were from the CHLC database and the Genome Database (GDB). Genotyping of CHLC markers was performed by Research Genetics Inc. PCR of GDB markers was carried out in a 15 $\mu$l volume containing 60 ng DNA, 375 $\mu$M dATP, dCTP, dGTP and dTTP, 5 $\mu$M each primer (the forward primer was labelled with either 6-Fam or Tet fluorescent dye), 2.5 mM MgCl$_2$, 1/10 volume of 10X PCR buffer II (PE Applied Biosystems) and 0.6 units AmpliTaq Gold polymerase (PE Applied Biosystems). Samples were amplified on a Hybaid OmniGene thermal cycler using the heated lid. The following profile was used for DNA amplification: 95° C. for 12 minutes; 10 cycles of 15 s at 94° C., 15 s at 55° C., 30 s at 72° C.; 20 cycles of 15 s at 89° C., 15 s at 55° C., 30 s at 72° C; 30 min at 72° C. and 30 min at 35° C. Samples were diluted 1/10 in dH$_2$O, and 1.5 $\mu$l was added to the dye loading mix (2.5 $\mu$l formamide, 0.5 $\mu$l blue dextran [50 mM EDTA, 50 mg/ml blue dextran], 0.5 $\mu$l GS500 Tamra size standard (PE Applied Biosystems). 1.5$\mu$l of each sample was loaded onto a 4% denaturing polyacrylamide gel and electrophoresed on ABI377 sequencers. Products were detected using the Genescan program, version 2.0.2 (PE Applied Biosystems) and alleles assigned using the Genotyper program, version 1.1.1 (PE Applied Biosystems). All genotyping was carried out by individuals blind to clinical diagnosis.

Chromosome 4q35 markers used, and the distance between them (in cM) as obtained from http://cedar.genetics.soton.ac.uk/pub/chrom4/gmap in the direction from centromere to q terminus were: D4S2417-9.2-D4S2951-4.3-D4S3041-3.1-D4S1554-0.4-D4S2920-4.4-D4S2954-3.4-D4S1535-1.0-D4S408-4.7-D4S2924-2.5-D4S171-0.04-D4S3051-0.4-D4S3032-0.04-D4S426-1.7-D4S2930-0.003-D4S1652. D4S1652 is the most distally reported polymorphic microsatellite marker on 4q. Additional microsatellite, single nucleotide polymorphisms or VNTR markers within this region may also be used.

Primers used are shown in Table 1.

Statisticcl Analylsis

Two-point lod scores were calculated between each marker and the disease using the MLINK program of the LINKAGE package, version 5.2 (Lathrop et al. 1984). Two disease thresholds were analysed: Model I considered all BPI, BPII and SZ/MA individuals as affected whilst all other family members were regarded as unaffected. Model II considered all affected individuals from model I and all UP individuals as affected and all other family members as unaffected.

Two penetrance groups with maximum age-specific penetrance levels of either 60% or 90% and each containing four liability classes (1<20 years, 2=20–29 years. 3=30–39 years and 4$\geq$40 years) were used. Liability classes in the 90% penetrance group were defined with penetrance of 0.18. 0.45, 0.68 and 0.90, whilst those in the 60% group were defined with penetrance of 0.12, 0.30, 0.45 and 0.60. Both dominant and recessive models were analysed, with a disease allele frequency of 0.035 for the dominant model and 0.20 for the recessive model. Data was also analysed with the dominant model and disease allele frequencies of 0.10 and 0.20. Multi-point analysis was undertaken for the 15 markers studied on chromosome 4q35 using the LINKMAP program of the LINKAGE package. The diagnostic models and penetrance groups used were the same as for two-point analysis.

The HOMOG program (Ott 1991) was used to test for evidence of heterogeneity.

Three non-parametric methods of analysis in this study that are more suited to the larger-sized pedigrees found in the cohort were also used. These non-parametric analyses included the GENEHUNTER (Kruiglyak et al. 1995), MFLINK (Curtis and Sham 1995) and APM (Weeks and Lange 1988) programs. Non-parametric sib pair analyses (as has been typically done by other groups with smaller or nuclear pedigrees) has not been presented since the small number of independent sib pairs in the pedigree cohort do not provide sufficient statistical power to draw significant conclusions.

Results

Genome Scan

The 35 most informative individuals from Family 01 were subjected to an approximately 15 cM genome screen using 202 markers from the Weber (CHLC) 6 and 6a panels of microsatellite markers. Chromosome 16 was not genotyped as each of these individuals had previously been genotyped for 12 microsatellite markers (Adams et al. 1997). These 35 individuals were chosen from the entire pedigree for this initial screen as they provided sufficient power to detect linkage, the maximum lod score as determined by SLINK being 6.43. All data were analysed using the MLINK program of the LINKAGE package. Disease models I (narrow definition in which only BPI, BPII and SZ/MA were classified as affected) and II (broad definition in which BPI, BPII, SZ/MA and UP were classified as affected) were analysed with both dominant and recessive inheritance models using both 60% and 90% maximum age-specific penetrance levels. Using SLINK simulations, no markers from a 214 marker genome screen for a given genetic and diagnostic model were expected to give a lod score greater than 3.00 by chance and less than one marker was expected to give a lod score greater than 2.00 by chance. Two-point lod scores greater than 1.00 were obtained for 21 of the analysed markers for at least one diagnostic model, and four of these gave scores greater than 2.00. The four markers which gave lod scores greater than 2.00 were DIS518 (lod=2.42; model I, 90% dominant); D4S1652 (lod=2.39; model II, 90% dominant); D5S807 (lod =2.12; model II, 90% dominant) and D5S1470 (lod=2.92; model II, 90% dominant) and each was then analysed in more detail.

The 52 additional individuals in Family 01 for whom DNA samples are available were typed for the four markers which gave lod scores greater than 2.00, and two-point analysis of the entire family was undertaken. The lod score for D1S518 reduced from 2.42 to 0.20, thus eliminating chromosome 1 from further analysis. Lod scores for the two chromosome 5 markers, D5S807 and D5S1470, located approximately 31 cM apart, remained greater than 1.00 (Table 2). A further seven markers on chromosome 5p were analysed, one of which, D5S1492, gave a lod score of 1.00 (Table 2).

A Potential Susceptibility Locus at 4q35

The chromosome 4q35 marker D4S1652 was the only one whose lod score remained above 2.00 following typing of the entire family. A maximum lod score of 2.20 was obtained at θ=0.20 for model II with a dominant mode of inheritance and 90% maximum age-specific penetrance. Genotypes of the 87 pedigree members were obtained for a further 14 microsatellite markers spanning approximately 35 cM of the distal arm of chromosome 4q. Two-point analysis of the data revealed seven markers in an approximately 10 cm interval to have lod scores greater than 1.00 (Table 3), with D4S1652 still having the largest two-point score. To ascertain the robustness of these linkage results, marked changes were made to a number of model parameters including disease allele frequency, penetrance level and phenocopy rate, to determine how they affected the maximum lod scores. The lod scores for these markers were found to be relatively robust to these changes (Table 4) with all values remaining positive, supporting the presence of a susceptibility locus at chromosome 4q35.

Further Analysis of the 4q35 LOCUS

Three-point linkage analysis between sequential pairs of the fifteen 4q35 markers was undertaken using the LINK-MAP program of the LINKAGE package. A maximal score of 3.19 was obtained between D4S408 and D4S2924 for Model II with a dominant mode of inheritance and a maximum age-specific penetrance level of 90% (FIG. 1: solid line). This score was also robust, as lowering the maximum age-specific penetrance level to 60% still resulted in a maximum score of 3.19 (FIG. 1: dotted line). Although the lack of a clear genetic or diagnostic model results in multiple hypothesis testing, the consistent positive results for both the two-(Table 4) and three-point linkage analyses indicate a greater level of confidence in the data than if positive results were only to be found in some of the models tested.

Non-parametric methods of analysis were also used to examine the data. Further support was provided using the GENEHUNTER program (Kruglyak et al. 1996). Family 01 was too large for all 87 individuals to be analysed simultaneously, and had to be edited for GENEHUNTER to run. A maximum score of 2.62 (p=0.01) was obtained in the region spanning D4S1652 and D4S171. However, depending upon the way in which the pedigree was subdivided, the GENEHUNTER scores ranged from the high of 2.62 (p=0.01) to a low of 0.59 (p=0.16). The APM program (Weeks and Lange, 1988) also provided limited support for a locus at 4q35, with scores of 3.57 (p=0.0002) for f(q)=1 and 1.97 (p=0.0245) for f(q)=1/√q for D4S2924. Significant APM scores were not obtained for the other chromosome 4 loci. The MFLIWK program (Curtis and Sham 1995) was also used to analyse the data. A positive, but non-significant score of 1.43 was obtained between D4S171 and D4S2924.

Support for the 4q35 locus in other pedigrees

A further ten pedigrees in our cohort were genotyped for four microsatellite markers at chromosome 4q35 (D4S1652, D4S171, D4S2924, D4S408). Two-point linkage analysis of all eleven families using the broad diagnostic model (model II) with dominant inheritance and 90% maximum age-specific penetrance gave a maximum score of 2.03 at θ=0.20 at D4S1652 indicating that as a whole the additional 10 pedigrees do not provide additional support for, but also do not refute, the observation of linkage to chromosome 4q35. The lod score for D4S171 was 1.46 (θ=0.25), while scores for the other two markers were less than 1.00.

Of the additional pedigrees genotyped. Family 11 gave a lod score of 1.07 for muarker D4S1652 which was 100% of the maximum lod score that was expected from SLINK analysis thus indicating that linkage was possible in this family as well. Lod scores greater than 0.80 were also obtained for markers D4S171 and D4S408. So as to enable a preliminary disease haplotype to be constructed, members of Family 11 were genotyped for a further three markers at 4q35 (D4S2930, D4S426 and D4S3032) and positive lod scores were obtained: D4S426=1.08 (θ=0.00). D4S2930= 0.61 (θ=0.00) and D4S3032=0.14 (θ=0.20). Three-point analysis of Family 11 with the seven markers resulted in a maximum lod score of 1.16 between D4S2930 and D4S1652.

Small positive results were obtained in two additional families for the four markers (D4S1652, D4S171, D4S408 and D4S2924), but none of these were statistically significant or represented a major fraction of the maximum possible lod score when compared with the results obtained from simulation analysis (data not shown). Heterogeneity analysis with the HOMOG program (Ott 1991) showed statistically significant evidence for linkage of D4S1652 (p<0.05) and D4S171 (p<0.01) to BAD, but no statistically significant evidence for heterogeneity.

An additional 13 pedigrees were genotyped for six markers, D4S408, D4S2924. D4S171, D4S1652, D4S2954 and D4S1535. Two-point analysis of all families under broad diagnostic model with dominant inheritance and 90% maximum age-specific penetrance gave and maximum lod score of 1.44 at q=0.3 at D4S1652. The lod score for D4S171 was 1.15 at q=0.25, whilst scores of the other markers were less than 1.00.

In addition to Family 11 which is already highlighted in the description, linkage is likely in two other pedigrees. Family 12 and Family 19. SLINK analysis of Family 12 gives expected average and maximum lod scores of 0.4 and 0.67 (q=0.1) respectively. For Family 19 the average and expected lod scores were 0.42 and 1.02 respectively. The max lod scores obtained for Family 12 was 0.63 at q=0.1 at D4S1652 and 0.57 at q=0.1 at D4S2924 for Family 19.

Multipoint analysis of Family 12 gave maximum lod score of 0.8 between D4S1535 and D4S171. Multipoint analysis of Family 19 gave maximum score of 0.73 between D4S2924 and D4S171.

Discussion

A genome screen of 214 microsatellite markers in a large Australian BAD pedigree has led to the identification of a novel bipolar disorder susceptibility locus on chromosome 4q35, importantly, the positive lod scores obtained were robust to changes in the model with strong support for linkage even when a maximum age-specific penetrance level of 60% was used in the analysis (maximum multi-point lod score of 3.19 between D4S408 and D4S2924). Furthermore, increasing the disease allele frequency to as high as 0.20, or the occurrence of phenocopies to 0.10 still gave positive results at 4q$^3$5, thus substantiating the robustness of this finding. Results of the non-parametric analyses also provide support for this linkage result.

TABLE 1

Chromosome 4 microsatellite primers

| Primer name | Orientation | Primer sequence | |
|---|---|---|---|
| D4S1652 | Forward | 5' AAT CCC TGG GTA CAT TAT ATT TG 3' | (SEQ ID NO:1) |
| | Reverse | 5' CAG ACA TTC TTT ATT CTT TAC CTC C 3' | (SEQ ID NO:2) |
| D4S2930 | Forward | 5' CCT CAT GGT AGG TTA ATC CCA CG 3' | (SEQ ID NO:3) |
| | Reverse | 5' TAT TGA ATG CCC GCC ATT TG 3' | (SEQ ID NO:4) |
| D4S426 | Forward | 5' ATA CAC TGC ATC CAT ATA TAC AAG G 3' | (SEQ ID NO:5) |
| | Reverse | 5' ACA TTG TGA AAT GAC CAC AG 3' | (SEQ ID NO:6) |
| D4S3032 | Forward | 5' TGA AAT TCT ATT GAC CAA TGA TGT G 3' | (SEQ ID NO:7) |
| | Reverse | 5' TAG CAC CTG GAT TTA CCA TGA C 3' | (SEQ ID NO:8) |
| D4S3051 | Forward | 5' TTT GTT TGG TCT ATC AAA AGT C 3' | (SEQ ID NO:9) |
| | Reverse | 5' CAA GAT GTG CAG TGG G 3' | (SEQ ID NO:10) |
| D4S171 | Forward | 5' GGT CCA GTA AGA GGA CAG T 3' | (SEQ ID NO:11) |
| | Reverse | 5' TGG GTA AAG AGT GAG GCT G 3' | (SEQ ID NO:12) |
| D4S2924 | Forward | 5' AGT ATT GCA GTG CTT GGG 3' | (SEQ ID NO:13) |
| | Reverse | 5' CAT CCA CAG GGG ACA CAT TC 3' | (SEQ ID NO:14) |
| D4S408 | Forward | 5' GGT CTG ATG AAA ATG TTC TCA AGC 3' | (SEQ ID NO:15) |
| | Reverse | 5' TAG ACT GGG TTG TTA GGG ACT CTC 3' | (SEQ ID NO:16) |
| D4S1535 | Forward | 5' ACT TGT GAT ATA TAC CTG CCG 3' | (SEQ ID NO:17) |
| | Reverse | 5' TCT GAG AGC AGA ATG TTG AG 3' | (SEQ ID NO:18) |
| D4S2954 | Forward | 5' CCA TTT CAG TGT CTG TGA CTA 3' | (SEQ ID NO:19) |
| | Reverse | 5' GGA AGC CAA TTC CTC ATA 3' | (SEQ ID NO:20) |
| D4S2920 | Forward | 5' ACA CAG CAC AGT TTG TTT GA 3' | (SEQ ID NO:21) |
| | Reverse | 5' GAC CTG CCT AAG CCT TTG 3' | (SEQ ID NO:22) |
| D4S1554 | Forward | 5' CTT GTT TCC TGT TGA GCA CT 3' | (SEQ ID NO:23) |
| | Reverse | 5' GAA TGA TGT ACT GAT CAC CCA GAT 3' | (SEQ ID NO:24) |
| D4S3041 | Forward | 5' AAT CCC TAG GCA AAT ACC AT 3' | (SEQ ID NO:25) |
| | Reverse | 5' TCT TGA GTG GCT GAA ACT ACA T 3' | (SEQ ID NO:26) |
| D4S2951 | Forward | 5' TCG AGA TCG TGC CAT T 3' | (SEQ ID NO:27) |
| | Reverse | 5' CCC CAA GAT TAT TCT TAG ACT TT 3' | (SEQ ID NO:28) |
| D4S2417 | Forward | 5' AGC ACA AGA TTC TCT AAG CCC 3' | (SEQ ID NO:29) |
| | Reverse | 5' AAA GCC AAA AGA TGA TGC AA 3' | (SEQ ID NO:30) |

TABLE 2

Lod scores for the entire 87 member pedigree for chromosome 5q markers. Linkage analysis was performed using affection status model II.

| Marker | 90% dominant | 60% dominant | 90% recessive | 60% recessive |
|---|---|---|---|---|
| D5S392 | −10.34 | −1.28 | −3.65 | −0.57 |
| D5S1492 | 1.00 | 0.80 | 0.79 | 0.72 |
| D5S2505 | 0.33 | 0.61 | 0.74 | 0.60 |
| D5S807 | 1.10 | 0.73 | 0.89 | 0.70 |
| D5S817 | −2.25 | −0.19 | −0.11 | −0.05 |
| D5S1473 | 0.66 | 0.17 | 0.29 | 0.16 |
| D5S819 | 0.47 | 0.12 | 0.47 | 0.18 |
| D5S1470 | 1.03 | 0.41 | 0.43 | 0.42 |
| D5S2494 | −1.94 | 0.12 | 0.23 | 0.17 |

TABLE 3

Two-point lod scores for Family 1 for chromosome 4q35 markers using model I (narrow disease definition) and model II (broad disease definition) for dominant transmission with maximum age-specific penetrance levels of 60% and 90%. Lod scores greater than 1.00 are indicated by bold type.

| Locus | Recombination fraction | | | | | | | | | |
|---|---|---|---|---|---|---|---|---|---|---|
| | 0.00 | | 0.05 | | 0.10 | | 0.15 | | 0.20 | |
| Penetrance | 90% | 60% | 90% | 60% | 90% | 60% | 90% | 60% | 90% | 60% |
| Model 1 | | | | | | | | | | |
| D4S2417 | −3.89 | −2.18 | −2.08 | −1.18 | −1.33 | −0.76 | −0.86 | −0.49 | −0.55 | −0.31 |
| D4S2951 | −2.54 | −1.35 | −0.91 | −0.24 | −0.28 | 0.12 | 0.07 | 0.27 | 0.25 | 0.33 |
| D4S3041 | 0.22 | 0.03 | 0.19 | 0.00 | 0.15 | 0.03 | 0.11 | 0.05 | 0.07 | 0.06 |
| D4S1554 | −3.45 | −1.12 | −1.45 | −0.45 | −0.77 | −0.20 | −0.41 | −0.07 | −0.20 | −0.01 |
| D4S2920 | 0.54 | 0.48 | 0.51 | 0.42 | 0.46 | 0.36 | 0.41 | 0.29 | 0.34 | 0.23 |
| D4S2954 | −1.54 | −1.26 | −0.72 | −0.74 | −0.46 | −0.53 | −0.32 | −0.39 | −0.23 | −0.29 |
| D4S1535 | −1.19 | −0.73 | −0.36 | −0.25 | −0.11 | −0.08 | 0.01 | −0.01 | 0.07 | 0.02 |
| D4S408 | −3.66 | −1.30 | −1.50 | −0.57 | −0.81 | −0.28 | −0.44 | −0.14 | −0.22 | −0.06 |
| D4S2924 | −0.31 | −0.30 | −0.30 | −0.26 | −0.29 | −0.22 | −0.26 | −0.17 | −0.21 | −0.12 |
| D4S171 | −6.12 | −1.69 | −2.75 | −0.91 | −1.65 | −0.55 | −1.02 | −0.34 | −0.61 | −0.21 |
| D4S3051 | −0.26 | −0.18 | −0.26 | −0.15 | −0.25 | −0.12 | −0.21 | −0.08 | −0.15 | −0.05 |
| D4S3032 | 0.08 | 0.13 | 0.08 | 0.11 | 0.08 | 0.08 | 0.08 | 0.06 | 0.06 | 0.04 |
| D4S426 | −0.29 | −0.24 | −0.28 | −0.21 | −0.27 | −0.18 | −0.24 | −0.14 | −0.20 | −0.10 |
| D4S2930 | −6.51 | −1.87 | −3.00 | −1.08 | −1.78 | −0.68 | −1.09 | −0.44 | −0.66 | −0.28 |
| D4S1652 | −6.50 | −1.93 | −2.60 | −1.05 | −1.43 | −0.63 | −0.80 | −0.37 | −0.42 | −0.22 |
| Model 2 | | | | | | | | | | |
| D4S2417 | −6.30 | −2.18 | −3.06 | −1.68 | −1.96 | −1.17 | −1.29 | −0.80 | −0.83 | −0.53 |
| D4S2951 | −6.72 | −3.97 | −4.40 | −2.60 | −2.98 | −1.93 | −2.04 | −1.42 | −1.37 | −0.99 |
| D4S3041 | −1.15 | −0.65 | −0.93 | −0.57 | −0.76 | −0.49 | −0.60 | −0.40 | −0.47 | −0.31 |
| D4S1554 | −2.91 | −2.04 | −1.02 | −0.77 | −0.29 | −0.26 | 0.11 | 0.01 | 0.32 | 0.14 |
| D4S2920 | −1.64 | −0.97 | −1.30 | −0.78 | −1.03 | −0.64 | −0.81 | −0.51 | −0.63 | −0.41 |
| D4S2954 | −2.67 | −1.89 | −1.46 | −1.32 | −0.99 | −0.92 | −0.69 | −0.63 | −0.46 | −0.41 |
| D4S1535 | −0.19 | −0.40 | 0.73 | 0.18 | 0.98 | 0.39 | 1.06 | 0.47 | 1.04 | 0.47 |
| D4S408 | −0.39 | −0.04 | 1.27 | 0.87 | 1.66 | 1.13 | 1.75 | 1.17 | 1.67 | 1.10 |
| D4S2924 | 0. | 1.29 | 1.00 | 1.23 | 1.04 | 1.13 | 0.99 | 1.01 | 0.88 | 0.86 |
| D4S171 | −0. | 0.74 | 1.34 | 1.38 | 1.87 | 1.55 | 2.03 | 1.56 | 1.98 | 1.45 |
| D4S3051 | 0.92 | 1.45 | 1.22 | 1.35 | 1.22 | 1.23 | 1.14 | 1.09 | 1.00 | 0.92 |
| D4S3032 | −0.43 | −0.49 | −0.22 | −0.33 | −0.10 | −0.22 | −0.02 | −0.14 | 0.02 | −0.09 |
| D4S426 | 0.60 | 1.24 | 0.93 | 1.18 | 0.98 | 1.09 | 0.94 | 0.97 | 0.84 | 0.83 |
| D4S2930 | −1.57 | 0.51 | 0.63 | 1.15 | 1.28 | 1.34 | 1.53 | 1.37 | 1.57 | 1.28 |
| D4S1652 | −0.02 | 1.68 | 1.76 | 2.02 | 2.15 | 2.02 | 2.20 | 1.89 | 2.07 | 1.69 |

TABLE 4

Variation in lod scores with changes in model parameters

| Variable | D4S1652 | D4S171 | D4S2924 | D4S408 |
|---|---|---|---|---|
| Normal* | 2.20 | 2.03 | 1.04 | 1.75 |
| Phenocopy 1% | 2.16 | 2.07 | 1.00 | 1.77 |
| Phenocopy 10% | 1.15 | 1.48 | 0.21 | 1.42 |
| Disease frequency 10% | 2.21 | 2.03 | 1.04 | 1.75 |
| Disease frequency 20% | 2.22 | 2.05 | 1.04 | 1.74 |
| Max penetrance 30% | 1.53 | 1.03 | 1.30 | 0.56 |
| Max penetrance 12% | 1.00 | 0.61 | 1.02 | 0.25 |

*Normal = 90% maximum penetrance, disease allele frequency of 3.5% and 0.5% phenocopy rate References Adams L J, Salmon J A, Kwok J B, Vivero C, Donald J A, Mitchell P B, Schofield P R (1997) Exclusion of linkage between bipolar affective disorder and chromosome 16 in 12 Australian pedigrees. Am J Med Genet 74: 304–310.

Berrettini. W. H. et al. Chromosome 18 DNA markers and manic depressive illness: evidence for a susceptibility gene. Proc. Natl. Acad. Sci USA 91, 5918–5921 (1994).

Blackwood. D. H. R. et al. A locus for bipolar affective disorder on chromosome 4p. Nat. Genet. 12, 427–430 (1996).

Coon, H. et al. Analysis of chromosome 18 DNA markers in multiplex pedigrees with manic depression. Biol. Psychiatry 39, 669–696 (1996).

Curtis D. Sham P C (1995) Model-free linkage analysis using likelihoods. Am J Hum Genet 57: 703–716.

De bruyn. A. et al., Linkage analysis of families with bipolar illness and chromosome 18 markers. Biol. Psychiatry 36, 679–688 (1996). Gurling. H. et al. Linkage findings in bipolar disorder. Nat. Genet. 10, 8–9 (1995).

Freimer. N. B., et al. (1996) Genetic mapping using haplotype, association and linkage methods suggests a locus for severe bipolar disorder (BPI) at 18q22-q23. Nat. Genet. 12, 436–441.

Kruglyak L. et al. (1996) Parametric and nonparametric linkage analysis: a unified mid point approach. Am J Hum Genet 58: 1347–1363.

Lathrop, G. M., et al., Strategies for multilocus linkage analysis in humans. Proc. Natl. Acad. Sci USA 81, 3443–3446.

Mitchell P., et al. (1991) Close linkage of bipolar disorder to chromosome 11 markers is excluded in two large Australian pedigrees. J Affective Disord 21: 23–32.

Nurnberger J. I. Jr, et al. (1994) Diagnostic interview for genetic studies. Rationale. unique features, and training. NIMH Genetics Initiative. Arch Gen Psych 51: 849–859.

Ott, J. Computer-simulation methods in human linkage analysis. Proc. Natl. Acad. Sci. USA 86, 4175–4178 (1989).

Stine, O. C. et al. Evidence for linkage of bipolar disorder to chromosome 18 with a parent-of-origin effect. Am. J. hum. Geiiet. 57, 1384–1394 (1995).

Straub. R. E. et al. A possible vulnerability locus for bipolar affective disorder on chromosome 2lq22.3. *Nat. Genet.* 8. 291–296 (1994).

Weeks, D. E. & Lange, K. The affected-pedigree-member method of linkage analysis. *Am. J. hum. Genet.* 42, 315–316. D Weeks, D. E., et al. SLINK: a general simulation program for linkage analysis. *Am. j. hum. Genet* 47, A204 (supplement) (1990).

What is claimed is:

1. A method of assessing an individual's predisposition to bipolar affective disorder (BAD), comprising detecting the presence or absence of at least one BAD-linked allele at 4q35 on chromosome 4 of said individual wherein the presence of a BAD-linked allele is indicative of a individual's predisposition to BAD.

2. A method according to claim 1, wherein the BAD-linked allele is a microsatellite allele.

3. A method according to claim 1, wherein the BAD-linked allele is from locus D4S 1652, D4S408, D4S 171, and D4S2924.

4. A method according to claim 1, wherein said at least one BAD-linked allele is detected by PCR and gel electrophoresis.

* * * * *